(12) United States Patent
Lefevre et al.

(10) Patent No.: US 6,448,233 B1
(45) Date of Patent: Sep. 10, 2002

(54) TOPICAL APPLICATION OF A COMBINATION OF BENZOYL PEROXIDE AND A SECOND ACTIVE INGREDIENT

(75) Inventors: Jean Marie Lefevre, Amiens (FR); Luppo Edens, Rotterdam (NL)

(73) Assignee: Cosmoferm B.V. (NL)

( * ) Notice: Subject to any disclaimer, the term of this patent is extended or adjusted under 35 U.S.C. 154(b) by 0 days.

(21) Appl. No.: 09/462,384

(22) PCT Filed: Jul. 8, 1998

(86) PCT No.: PCT/EP98/05046
§ 371 (c)(1),
(2), (4) Date: Mar. 21, 2000

(87) PCT Pub. No.: WO99/02133
PCT Pub. Date: Jan. 21, 1999

(30) Foreign Application Priority Data

Jul. 8, 1997 (EP) .............................................. 97202096

(51) Int. Cl.⁷ ................................................ A61K 31/70
(52) U.S. Cl. .............................. 514/31; 514/24; 514/29; 514/714; 514/859
(58) Field of Search ............................ 514/29, 859, 31, 514/24, 714

(56) References Cited

U.S. PATENT DOCUMENTS 4,497,794 A    2/1985  Klein et al. .................... 514/29
5,538,732 A    7/1996  Smith et al.

FOREIGN PATENT DOCUMENTS

| | | |
|---|---|---|
| CA | 2 015 111 | 10/1991 |
| DE | 43 14 549 A1 | 11/1993 |
| GB | 2 088 717 | 6/1982 |
| WO | WO 93 15726 | 8/1993 |
| WO | WO 97 11680 | 4/1997 |
| WO | WO 97 27841 | 8/1997 |

OTHER PUBLICATIONS

Brisaert et al., 1996 Pharm. World Sci. 18: 182–186.

Chellquist et al., 1992 Pharm. Res. 9: 1341–1346.

Eady et al., 1993 Br. Med. J. 306: 555–556.

Eady et al., 1989 Br. J. Dermatol. 121: 51–57.

*Primary Examiner*—Elli Peselev
(74) *Attorney, Agent, or Firm*—Morrison & Foerster LLP

(57) ABSTRACT

Disclosed herein is a dispensing system for benzoyl chloride and an antimicrobial agent which antimicrobial agent is a macrolide or an aminoglycoside antibiotic. The dispensing system comprises a first container containing a composition comprising benzoyl peroxide suspended in an aqueous solvent and further includes a viscosifying agent and a second container containing a second composition, wherein the second composition comprises an antimicrobial agent in a solvent and further comprising a viscosifying agent. The solvent is present in a concentration which is too high for direct application.

7 Claims, No Drawings

TOPICAL APPLICATION OF A COMBINATION OF BENZOYL PEROXIDE AND A SECOND ACTIVE INGREDIENT

This application is a 371 of PCT/EP98/05046 filed Jul. 8, 1998.

FIELD OF THE INVENTION

The present invention relates to the field of topical application of a combination of incompatible active ingredients, one being benzoyl peroxide.

BACKGROUND OF THE INVENTION

Acne vulgaris is a skin disorder frequently occurring in young people. It is a disorder of the sebaceous follicles and is associated with the sharp increase in androgen production during adolescence. Hyperproduction of sebum and inflammation caused by proliferation of Propionibacterium acne are associated with this skin disorder.

Erythromycin, or a mixture of erythromycin and clindamycin, is commonly used for the treatment of acne.

However, propionibacterial resistance to these antibiotics is a growing concern because of its high incidence (Eady et al. (1993), Br. Med. J. 306: 555–556), the resistance to high concentrations of erythromycin and the cross resistance to clindamycin (Eady et al. (1989), Br. J. Dermatol. 121: 51–57). One way to minimize the. selective pressure towards resistancies is to combine the antibiotic with benzoyl peroxide.

Benzoyl peroxide is clinically effective because of its bactericidal activity against Propionibacterium acnes as well as through its mild keratinolytic effect.

Unfortunately, several factors hamper the development of convenient topical formulations containing both erythromycin as well as benzoylperoxide.

For example, erythromycin can be stably formulated only in high concentrations of suitable solvents such as ethanol (Brisaert et al. (1996), Pharm. World Sci. 18: 182–186), whereas stability in formulations containing high levels of water is unacceptably low. However, topical application of high concentrations of ethanol is undesirable because of its irritancy to the skin.

In contrast, the stability of benzoyl peroxide in solvents like ethanol is low. Long term stability of benzoyl peroxide can only be guaranteed in compositions providing a low benzoyl peroxide solubility (Chellquist and Gorman (1992), Pharm. Res. 9: 1341–1346). In addition, benzoyl peroxide is extremely reactive, because of instability of the O—O bond. Consequently, benzoyl peroxide can be expected to have a deleterious effect on the chemical stability of other compounds mixed with benzoyl peroxide.

Currently, for topical application of a combination of benzoyl peroxide and erythromycin, a suitable solvent has to be added to both compounds being individually packed as a powder, whereupon the resulting solution in turn has to be mixed into a topical gel. It is highly desirable to avail of a less cumbersome method to apply these compounds.

DESCRIPTION OF THE INVENTION

The present invention provides a convenient solution to the above problems by applying a multicompartment dispensing system to enable separate containment of individual compositions, i.e. a first composition comprising benzoyl peroxide and a second composition comprising a second active ingredient. According to the invention, said first and second composition generate a final composition when mixed upon delivery, said final composition being effective to apply benzoyl peroxide as well as the second active ingredient in an effective form. The mixing of the individual compositions thereby may occur either in situ or in the dispensing system prior to delivery.

The present invention further discloses a method to produce an effective composition comprising benzoyl peroxide and a second active ingredient by in situ mixing of two individual compositions, each comprising a predetermined amount of either benzoyl peroxide or a second active ingredient.

The use of a multicompartment dispensing system according to the invention enables the preparation and use of separate compositions, on the one hand a composition comprising benzoyl peroxide as the active ingredient and on the other hand a composition comprising a second active ingredient. These separate compositions are prepared in such a way that the individual requirements for stable formulation of each active ingredient are fulfilled. In addition, the separate compositions are prepared in such a way that the final composition is effective to deliver the active ingredients present in each individual composition in a form suitable and effective for direct application.

Thus, the nature of the first and second composition are determined by on the one hand the stability requirements is of each individual active ingredient and on the other hand the desired properties of the final composition.

The second active ingredient is an ingredient which may act in concert with or even synergistically with benzoyl peroxide. Said second active ingredient for instance may be an antimicrobial agent, preferably an antibacterial or antifungal agent. More preferably, said antimicrobial agent is a macrolide antibiotic, such as erythromycin or natamycin, and/or an aminoglycoside antibiotic, such as clindamycin or lincomycin. Another example of an antimicrobial agent which may be combined with benzoyl peroxide is a sphingoid base, like sphingosine or phytosphingosine (Bibel et, al (1992), J. Invest, Dermatol. 98: 269–273).

Typically, a stable composition may be obtained when an active ingredient is formulated as a suspension formulation, e.g. a composition wherein the vehicle is selected to provide a low solubility of the active ingredient. Sedimentation of a suspended active ingredient in a suspension formulation is prevented by the use of a suitable viscosifying or thickening agent. A stable composition of the active ingredient further may be obtained using a high concentration of a non-aqueous solvent in said composition. Examples of such non-aqueous solvents are ethanol or hydric solvents like polyethylene glycol, butylene glycol, propylene glycol or glycerol. A stable composition of the active ingredient further may be obtained by dissolving a high concentration of the active ingredient in the solvent of choice.

The viscosity of the individual compositions is adjusted to the desired level using a viscosifying or thickening agent. The concentration of the viscosifying agent used mainly is determined by the solvent, the pH, and the weight and size of the particles to be kept in suspension. Conveniently, the concentration of the viscosifying agent may range from 0.1–3%. Desirable viscosities may range from 100 to 30.000 cps (Brookfield, 25° C.–25 rpm), preferably from 1000 to 10.000 cps. It is preferred that the two individual compositions present in the dispenser according to the invention have a substantially similar viscosity.

Examples of viscosifying agents for gellifying an aqueous suspension composition include Carbomer viscosifiers like Carbopol 940 (B.F. Goodrich) and cellulose derivatives like hydroxypropylmethylcellulose, optionally in combination with colloidal magnesium silicate (Veegum). To stabilize suspensions containing particles and/or containing high concentrations of ethanol or hydric solvents like polyethylene glycol, butylene glycol, propylene glycol or glycerol, viscosifying agents which may be considered include xanthans, Carbomer viscosifyers like Carbopol Ultrez 10 or carrageenans like Satia gum UTC 30 (SBI, Benelux).

The concentration of the active ingredient in the stable composition typically depends on both the desired end concentration of said active ingredient in the final composition as well as on the ratio wherein the first and second composition are mixed to obtain the final composition.

The ratio in which the two individual compositions are delivered by the dispensing system can be adjusted as desired. Typically, said ratio may be adjusted to any value within a range varying from 1:1 to 1:50. Preferably, said ratio may vary from 1:2 to 1:20.

To obtain a dilution of one composition into the other is especially advantageous in the case that one composition contains a solvent in a concentration which is to high for direct topical application.

A suitable benzoyl peroxide composition for use in the dispensing system according to the invention is for instance an aqueous suspension formulation comprising benzoyl peroxide in a concentration ranging from 2 to 30% (w/v).

Suitable formulations guaranteeing long term stability of benzoyl peroxide compositions at elevated temperature conditions are. given by e.g. Chellquist and Gorman (supra) and Bollinger et al. (J. Pharm. Sci. 66 (1977): 718–722).

Typically, end concentrations of benzoyl peroxide on the skin may range from 2% to 15%.

The nature of the composition comprising the second active ingredient will depend on the requirements for stable formulation of the second active ingredient.

Stable erythromycin compositions are for instance specified by Vandenbossche et al. (Int. J. Pharmaceutics, 67 (1991): 195–199). For long term stability at elevated temperatures erythromycin compositions containing high levels of ethanol are preferable (Brisaert et al. (1994), Farmaceutisch Tijdschrift voor België, 1–2, 2–5). The use of pure ethanol as a solvent for erythromycin is also advantageous because erythromycin base can be dissolved in concentrations up to 30%. Alternatively, stable erythromycin compositions are suspension formulations of erythromycin, suspended in for instance propylene glycol, PEG 400, isopropanol, or mixtures thereof.

Stable aqueous natamycin compositions are described for instance in European Patent Application EP 678241. The stable natamycin compositions disclosed in EP 678241 are suspensions of natamycin crystals in an aqueous medium, wherein sedimentation of the crystals is prevented by the addition of a suitable viscosifying agent, such as xanthan or carrageenan. Additional suitable viscosifyers include Carbomers or related resins.

Stable aqueous clindamycin compositions are for instance specified by Oesterling (J.Pharm. Sciences (1970) 59: 63–67). Using clindamycin, maximum stability is obtained at a pH value of 3–5.

The nature of the final composition further may determine additional properties of one or both individual composition(s). For instance, the pH of the benzoyl peroxide composition and/or the composition comprising the second active ingredient may be adjusted to the desired pH value of the final composition.

In a preferred embodiment of the invention, a multicompartment dispenser is provided containing a first composition comprising benzoyl peroxide and a second composition comprising erythromycin. Said first composition comprises 5% (w/v) benzoyl peroxide suspended in an aqueous composition adjusted with sodium hydroxide to a pH of 8–8.5 and comprising Carbopol 940 as a viscosifying agent to reach a Brookfield viscosity between 500 and 5000 cps. Said second composition comprises 30% (w/v) erythromycin dissolved in 96% ethanol and Carbopol Ultrez 10 as a viscosifyer. Preferably, the viscosity of the erythromycin composition is comparable to the viscosity of the benzoyl peroxide gel. Said first and second composition are mixed in a ratio of nine parts first to one part second composition, resulting in a final composition having a concentration of about 5% benzoyl peroxide and 3% erythromycin. In this embodiment, the nature of the erythromycin composition, i.e. dissolved in 96% ethanol, specifically requires a delivery ratio of both compositions which ensures a dilution of said erythromycin composition in the final composition of at least about a factor 10.

Since erythromycin is more active at an alkaline pH (Heilman and Herrell (1952), Proc. Staff Meetings Mayo Clinic 27: 285–304), the adjustment of the pH to a value of about 8.5 is desirable for optimal activity. However, this pH value has a deleterious effect on erythromycin stability. The use of a dispenser according to the invention ensures that this pH adjustment occurs only after delivery from the dispenser and mixing on the skin, whereby the final pH is brought about by the benzoyl peroxide composition.

In a further embodiment of the invention, the second composition comprises natamycin as the active ingredient.

The solubility of natamycin, and thus its antifungal effectiveness, is optimal in the higher or lower pH ranges, e.g. around pH 3. Contrary, its stability in these pH ranges is rather low. Therefore, the use of a dispenser according to the invention allows for the combination of a concentrated stable natamycin composition with a stable but acidic benzoyl peroxide composition.

The dispensing system used is not critical to the invention. The present invention contemplates any dispensing system which allows for a separate containment as well as a simultaneous dosing (dispensing) of the individual compositions. Examples of suitable dispensing systems are given in WO 97/27841. A preferred multicompartment dispensing system is a dispenser containing two differently-sized compartments. Such a dispenser enables the dispensing of unequal amounts of two different compositions.

Care should be taken to use metal parts which are teflon-coated or nylon-coated (Rilsan process), since benzoyl peroxide is a rather corrosive compound.

The dispensing system according to the invention provides a covenient way to topically deliver a combination of benzoyl peroxide and a second active ingredient.

EXAMPLE 1

Topical Application of Benzoyl Peroxide and Erythromycin

Benzamycin® is a pharmaceutical product marketed by Dermik (USA) against serious forms of acne. The product consists of a mixture of 3% erythromycin and 5% benzoyl peroxide. Owing to the chemical imcompatability of erythromycin and benzoyl peroxide, the product comes as two separate jars, one containing erythromycin and one containing a benzoyl peroxide gel. Prior to use, erythromycin and benzoyl peroxide have to be mixed and refrigerated to allow a maximal use period of 3 months by the patient.

A two chamber dispenser was supplied by CosmoCair (Gist-brocades, Delft, the Netherlands). This "Symbio" dispenser combines in one housing a normal and an air-free lotion pump, both activated by the same actuator. Each one of the two pumps is connected to its own individual chamber. The air-free lotion pump is connected with a small cartridge equipped with a plunger in the bottom of the cartridge. The other pump is connected with a diptube and dispenses the formulation from the largest chamber. When the dispenser is assembled, the filled cartridge is (partly) submerged in the formulation contained in the largest chamber. During storage and use, the formulations contained in the cartridge and the largest chamber are kept completely separated.

Upon actuation, the dispenser delivers 0.4 grams of formulation, approx. 0.36 ml from the largest chamber and 0.04 ml from the cartridge. Both product streams are kept completely separated until they are ejected from the orifices of the dispenser.

To mimic Benzamycin® in terms of final concentrations of benzoyl peroxide and erythromycin on the skin, stable formulations of benzoyl peroxide and erythromycin were used to fill the two compartments of the Symbio dispenser.

To prepare a slightly viscous suspension of benzoyl peroxide, 2.0 grams of Carbopol Ultrez 10 (B.F. Goodrich) was carefully added to 450 ml of water. Subsequently 60 grams of aceton were added as well as 43.7 grams of benzoyl peroxide (Genfarma, the Netherlands). Using 8N NaOH, the pH of the solution was raised to pH 8.0 and water was added to obtain a final volume of 600 grams. Finally the suspension was homogenized with an Ultra-turrax. The next morning the suspension was centrifugated for 10 minutes at 5000 rpm in a Sorvall centrifuge to remove any air bubbles, if necessary carefully homogenized again and filled in the largest chamber of the dispenser.

To prepare a 10-times concentrated solution of erythromycin, 20 grams butylene glycol, 1.0 grams Carpobol Ultrez 10 and 49 grams of absolute ethanol were added to a glass beaker. Subsequently 30 grams of erythromycin (Genfarma, the Netherlands) was added and the mixture was mixed at 40° C. until a clear solution was obtained. Finally this solution was centrifuged to remove any air bubbles and filled into a cartridge. To close the cartridge, the plastic plunger was applied in such a way that no residual air was left between the erythromycin concentrate and the plunger.

After attachment of the filled cartridge to the airfree micropump and assembly of the pumphead with the benzoyl peroxide filled container, the pump was primed to prepare for dispensing of the two formulations on the skin. Manual mixing of the erythromycin concentrate with the co-dispensed benzoyl peroxide on the skin yielded a mixture containing 3% erythromycin and 5% benzoyl peroxide.

What is claimed is:

1. A dispensing system for benzoyl peroxide and an antimicrobial agent which antimicrobial agent is a macrolide or an aminoglycoside antibiotic, wherein said dispensing system comprises a first container containing a first composition consisting essentially of benzoyl peroxide suspended in an aqueous medium and further including a viscosifying agent, and a second container containing a second composition, said second composition consisting essentially of said antimicrobial agent in a solvent wherein said solvent is present in a concentration which is too high for direct topical application, and a viscosifying agent.

2. The dispensing system of claim 1 wherein the viscosity of the first composition and the second composition are substantially the same.

3. The dispensing system of claim 1 wherein the macrolide antibiotic is erythromycin or natamycin.

4. The dispensing system of claim 1 wherein said aminoglycoside antibiotic is clindamycin or lincomycin.

5. The dispensing system of claim 1 wherein the solvent is ethanol.

6. The composition of claim 1 wherein the ratio of the first composition to the second composition ensures a dilution of the second composition when the first composition and second composition are mixed of at least a factor of 10.

7. A method to produce a treatment formulation for topical delivery comprising benzoyl peroxide and an antimicrobial agent which is a macrolide or an aminoglycoside antibiotic which method comprises mixing at the location of topical delivery a first composition which consists essentially of benzoyl peroxide in an aqueous medium in the presence of a viscosifying agent and a second composition which consists essentially of said antimicrobial agent in a solvent wherein said solvent is present in a concentration which is too high for direct topical application, and a viscosifying agent.

* * * * *